US 6,400,974 B1

(12) United States Patent
Lesho (10) Patent No.: US 6,400,974 B1
(45) Date of Patent: Jun. 4, 2002

(54) IMPLANTED SENSOR PROCESSING SYSTEM AND METHOD FOR PROCESSING IMPLANTED SENSOR OUTPUT

(75) Inventor: Jeffery C. Lesho, Brookeville, MD (US)

(73) Assignee: Sensors for Medicine and Science, Inc., Germantown, MD (US)

(*) Notice: Subject to any disclaimer, the term of this patent is extended or adjusted under 35 U.S.C. 154(b) by 0 days.

(21) Appl. No.: 09/605,706

(22) Filed: Jun. 29, 2000

(51) Int. Cl.[7] .............................. A61B 5/05; A61B 5/00
(52) U.S. Cl. ...................... 600/347; 600/365; 600/345
(58) Field of Search ................................ 600/300–301, 600/345–365, 372, 385–390, 309, 316, 373, 377; 604/174–180; 128/903–904, 920

(56) References Cited

U.S. PATENT DOCUMENTS

| | | | |
|---|---|---|---|
| 3,229,684 A | | 1/1966 | Nagumo et al. |
| 3,576,554 A | | 4/1971 | Temps, Jr. et al. |
| 3,800,300 A | | 3/1974 | Van Oosterhout |
| 3,853,117 A | | 12/1974 | Murr |
| 3,872,455 A | | 3/1975 | Fuller et al. |
| 3,949,388 A | * | 4/1976 | Fuller ......................... 128/903 |
| 3,972,320 A | | 8/1976 | Kalman |
| 4,041,954 A | | 8/1977 | Ohara |
| 4,160,971 A | | 7/1979 | Jones et al. |
| 4,186,749 A | | 2/1980 | Fryer |
| 4,361,153 A | * | 11/1982 | Slocum et al. ............... 128/903 |
| 4,494,545 A | * | 1/1985 | Slocum et al. ............... 128/903 |
| 5,024,224 A | * | 6/1991 | Engebretson ............... 128/898 |
| 5,218,207 A | | 6/1993 | Rosenthal |
| 5,314,457 A | | 5/1994 | Jeutter et al. |
| 5,517,313 A | * | 5/1996 | Colvin, Jr. ................... 356/417 |
| 5,571,148 A | * | 11/1996 | Loeb et al. ................ 607/56 X |
| 5,630,836 A | | 5/1997 | Prem et al. |
| 5,682,149 A | | 10/1997 | Hofman |
| 5,735,887 A | | 4/1998 | Barreras, Sr. et al. |
| 6,175,752 B1 | * | 1/2001 | Say et al. ................ 600/365 X |
| 6,201,980 B1 | * | 3/2001 | Darrow et al. .............. 600/345 |

FOREIGN PATENT DOCUMENTS

| | | |
|---|---|---|
| GB | 2 235 496 A | 9/1999 |
| WO | WO 97/33513 A1 | 9/1997 |

OTHER PUBLICATIONS

Huang, Q., et al., "A 0.5–mW Passive Telemetry IC for Biomedical Applications", IEEE Journal of Solid State Cirucits, vol. 33, No. 7, Jul. 1998, pp. 937–945.

Hamici, Z., et al., "A High–Efficiency Power and Data Transmission System for Biomedical Implanted Electronic Devices", Meas. Sci. Technol., vol. 7, No. 2, 1996, pp. 192–201.

* cited by examiner

Primary Examiner—Kevin Shaver
Assistant Examiner—Navin Natnithithadha
(74) Attorney, Agent, or Firm—Rothwell, Figg, Ernst & Manbeck (57) ABSTRACT

A quantitative measurement system includes an external unit and an internal unit are provided for obtaining quantitative analyte measurements, such as within the body. In one example of an application of the system, the internal unit would be implanted either subcutaneously or otherwise within the body of a subject. The internal unit contains optoelectronics circuitry, a component of which may be comprised of a fluorescence sensing device. The optoelectronics circuitry obtains quantitative measurement information and modifies a load as a function of the obtained information. The load in turn varies the amount of current through coil, which is coupled to a coil of the external unit. A demodulator detects the current variations induced in the external coil by the internal coil coupled thereto, and applies the detected signal to processing circuitry, such as a pulse counter and computer interface, for processing the signal into computer-readable format for inputting to a computer.

17 Claims, 7 Drawing Sheets

IMPLANTED SENSOR PROCESSING SYSTEM AND METHOD FOR PROCESSING IMPLANTED SENSOR OUTPUT

BACKGROUND OF THE INVENTION

1. Field of the Invention

This invention relates to a circuit and method for processing the output of an implanted sensing device for detecting the presence or concentration of an analyte in a liquid or gaseous medium, such as, for example, the human body. More particularly, the invention relates to a circuit and method for processing the output of an implanted fluorescence sensor which indicates analyte concentration as a function of the fluorescent intensity of a fluorescent indicator. The implanted fluorescence sensor is a passive device, and contains no power source. The processing circuit powers the sensor through inductively coupled RF energy emitted by the processing circuit. The processing circuit receives information from the implanted sensor as variations in the load on the processing circuit.

2. Background Art

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source. An analyte is allowed to permeate the fluorescent matrix, changing the fluorescent properties of the indicator material in proportion to the amount of analyte present. The fluorescent emission is then detected and measured by the photodetector, thus providing a measure of the amount or concentration of analyte present within the environment of interest.

One advantageous application of a sensor device of the type disclosed in the '313 patent is to implant the device in the body, either subcutaneously or intravenously or otherwise, to allow instantaneous measurements of analytes to be taken at any desired time. For example, it is desirable to measure the concentration of oxygen in the blood of patients under anesthesia, or of glucose in the blood of diabetic patients.

In order for the measurement information obtained to be used, it has to be retrieved from the sensing device. Because of the size and accessibility constraints on a sensor device implanted in the body, there are shortcomings associated with providing the sensing device with data transmission circuitry and/or a power supply. Therefore, there is a need in the art for an improved sensor device implanted in the body and system for retrieving data from the implanted sensor device.

SUMMARY OF THE INVENTION

In accordance with the present invention, an apparatus is provided for retrieving information from a sensor device, comprising an internal sensor unit for taking quantitative analyte measurements, including a first coil forming part of a power supply for said sensor unit, a load coupled to said first coil, and a sensor circuit for modifying said load in accordance with sensor measurement information obtained by said sensor circuit; an external unit including a second coil which is mutually inductively coupled to said first coil upon said second coil coming into a predetermined proximity distance from said first coil, an oscillator for driving said second coil to induce a charging current in said first coil, and a detector for detecting variations in a load on said second coil induced by changes to said load in said internal sensor unit and for providing information signals corresponding to said load changes; and a processor for receiving and processing said information signals.

BRIEF DESCRIPTION OF THE DRAWINGS

The invention will be more fully understood with reference to the following detailed description of a preferred embodiment in conjunction with the accompanying drawings, which are given by way of illustration only and thus are not limitative of the present invention, and wherein:

FIGS. 5A–5e are diagrams of signals produced by the external data receiving unit;

DETAILED DESCRIPTION OF THE PREFERRED EMBODIMENT

Figure 1:
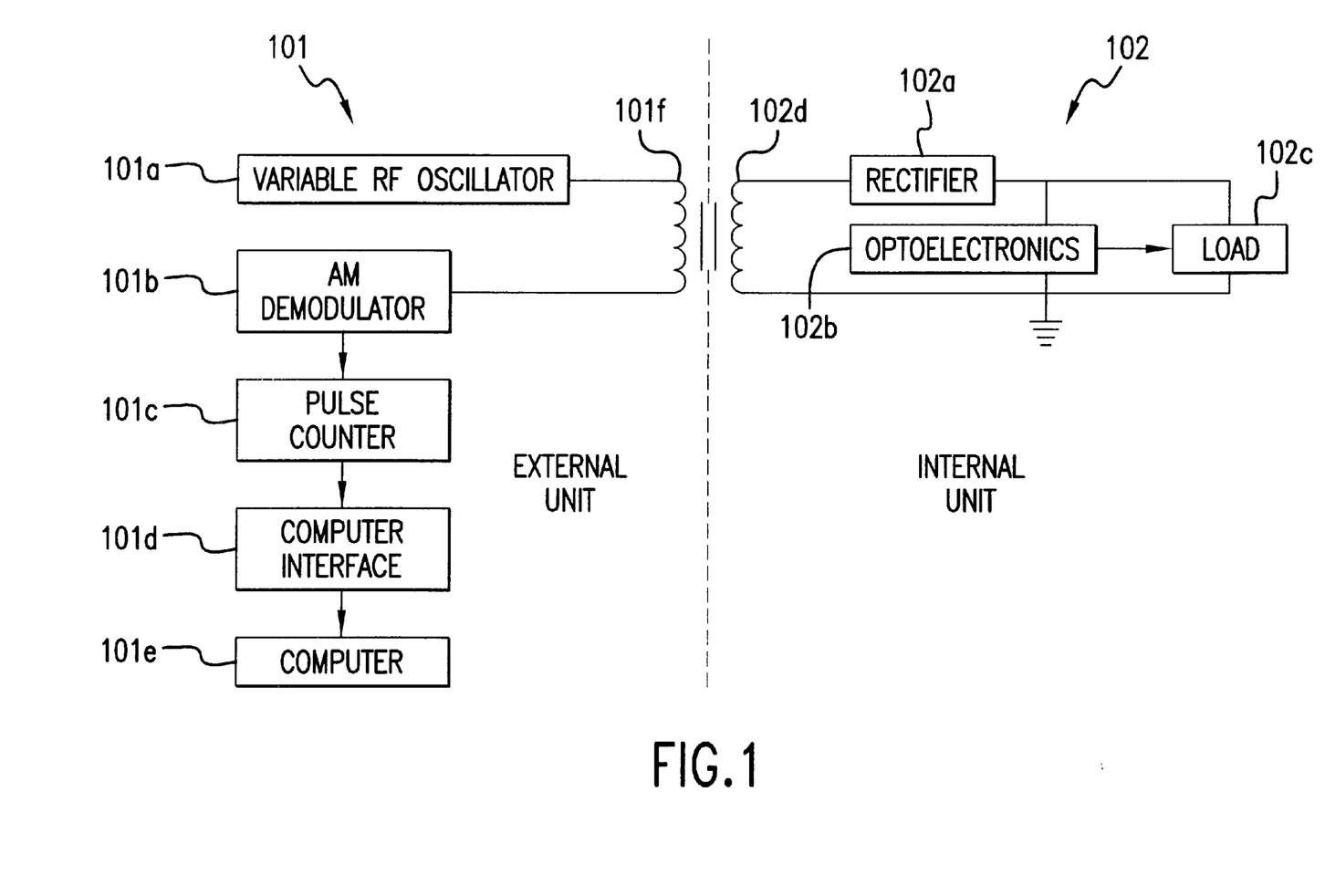
FIG. 1 is a block diagram of one preferred embodiment according to the present invention.

FIG. 1 shows a block diagram of one preferred embodiment of an implanted fluorescence sensor processing system according to the present invention.

The system includes an external unit 101 and an internal unit 102. In one example of an application of the system, the internal unit 102 would be implanted either subcutaneously or otherwise within the body of a subject. The internal unit contains optoelectronics circuitry 102b, a component of which may be comprised of a fluorescence sensing device as described more fully hereinafter with reference to FIGS. 6–8. The optoelectronics circuitry 102b obtains quantitative measurement information and modifies a load 102c as a function of the obtained information. The load 102c in turn varies the amount of current through coil 102d, which is coupled to coil 101d of the external unit. An amplitude modulation (AM) demodulator 101b detects the current variations induced in coil 101f by coil 102d coupled thereto, and applies the detected signal to processing circuitry, such as a pulse counter 101c and computer interface 101d, for processing the signal into computer-readable format for inputting to a computer 101e.

A variable RF oscillator 101a provides an RF signal to coil 101f, which in turn provides electromagnetic energy to coil 102d, when the coils 101f and 102d are within close enough proximity to each other to allow sufficient inductive coupling between the coils. The energy from the RF signal provides operating power for the internal unit 102 to obtain quantitative measurements, which are used to vary the load 102c and in turn provide a load variation to the coil 101f that is detected by the external unit and decoded into information. The load variations are coupled from the internal unit to the external unit through the mutual coupling between the coils 101f and 102d. The loading can be improved by tuning both the internal coil and the external coil to approximately the same frequency, and increasing the Q factor of the resonant circuits by appropriate construction techniques. Because of their mutual coupling, a current change in one coil induces a current in the other coil. The induced current is detected and decoded into corresponding information.

RF oscillator 101a drives coil 101f, which induces a current in coil 102d. The induced current is rectified by a rectifier circuit 102a and used to power the optoelectronics 102b. Data is generated by the optoelectronics in the form of a pulse train having a frequency varying as a function of the intensity of light emitted by a fluorescence sensor, such as described in the aforementioned '313 patent. The pulse train modulates the load 102c in a manner so as to temporarily short the rectifier output terminal to ground. This change in load causes a corresponding change in the current through the internal coil 102d, thereby causing a change in the magnetic field surrounding external coil 101f. This change in magnetic field causes a proportional change in the voltage across coil 101f, which is observable as an amplitude modulation. The following equation describes the voltage seen on the external coil:

$$V=I[Z+((\omega M)^2)/Zs] \quad (1)$$

where
V=voltage across the external coil
I=current in the external coil
Z=impedance of the primary coil
ω=frequency (rad/sec)
M=mutual inductance between the coils
Zs=impedance of the sensor equivalent circuit As shown by equation (1), there is a direct relationship between the voltage across the external coil and the impedance presented by the internal sensor circuit. While the impedance Zs is a complex number having both a real and imaginary part, which corresponds respectively to changes in amplitude and frequency of the oscillation signal, the system according to the present embodiment deals only with the real part of the interaction. It will be recognized by those skilled in the art that both types of interaction may be detected by appropriately modifying the external circuit, to improve the signal-to-noise ratio.

Figure 2:
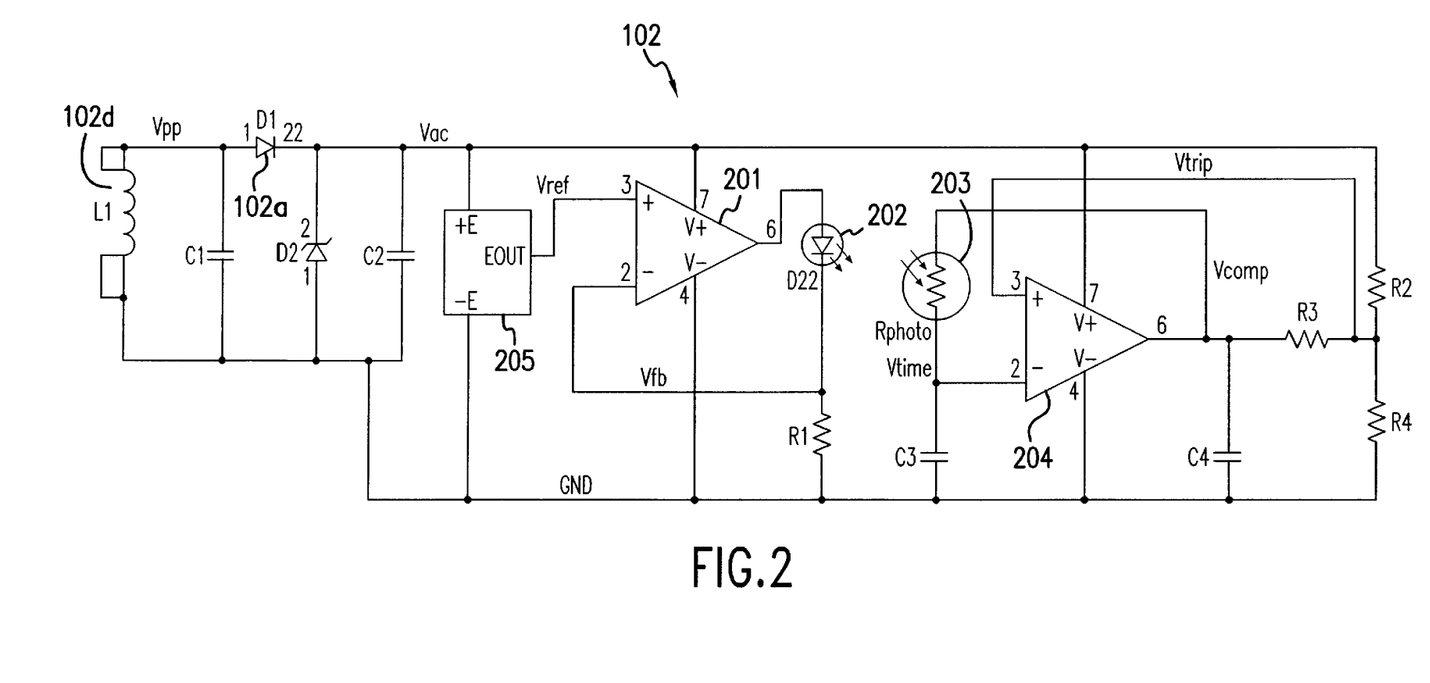
FIG. 2 is a schematic diagram of an internal sensor device unit according to one preferred embodiment of the invention.

FIG. 2 shows a schematic diagram of one embodiment of an internal sensor device unit according to the invention. The coil 102d (L1) in conjunction with capacitor C1, diode D1 (rectifier 102a) zener diode D2 and capacitor C2 constitute a power supply for the internal unit 102. Current induced in coil L1 by the RF voltage applied to external coil 101f by oscillator 101a (see FIG. 1) is resonated in the L-C tank formed by L1 and capacitor C1, rectified by diode D1, and filtered by capacitor C2. Zener diode D2 is provided to prevent the voltage being applied to the circuit from exceeding a maximum value, such as 5 volts. As is known by those skilled in the art, if the voltage across capacitor C2 starts to exceed the reverse breakdown voltage of the zener diode D2, diode D2 will start to conduct in its reverse breakdown region, preventing the capacitor C2 from becoming overcharged with respect to the maximum allowable voltage for the circuit.

Voltage regulator 205 receives the voltage from capacitor C2 and produces a fixed output voltage $V_{ref}$ to the noninverting input of operational amplifier 201. The output terminal of the operational amplifier 201 is connected to a light-emitting diode (LED) 202 connected in series with a feedback resistor R1. The inverting input terminal of operational amplifier 201 is supplied with the voltage across R1, to thereby regulate the current through LED 202 to $V_{ref}/R1$ (ignoring small bias current). Light emitted from LED 202 is incident on the sensor device (not shown) and causes the sensor device to emit light as a function of the amount of the particular analyte being monitored. The light from the sensor device impinges on the photosensitive resistor 203, whose resistance changes as a function of the amount of light incident thereon. Photoresistor 203 is connected in series with a capacitor C3, and the junction of the photoresistor and the capacitor C3 is connected to the inverting input terminal of comparator 204. The other end of photoresistor 203 is connected to the output terminal of the comparator 204 through a conductor $V_{comp}$. The output of the comparator 204 is also connected to a load capacitor C4 and a resistor network R2, R3 and R4. The comparator forms a variable resistance oscillator, with switching points determined by the values of R2, R3 and R4. C3 is a charge-up capacitor, which determines the base frequency of the oscillator for a given light level. This frequency is given by $$f=1/(1.38*Rphoto*C3) \quad (2)$$

$$Rphoto=R_{2fc}[10^{-\gamma \, log(a/2fc)}] \quad (3)$$

where
$R_{2fc}$(=24 kΩ) is the resistance of photoresistor 203 at 2 footcandles
γ(=0.8) is the sensitivity of the photoresistor
a=the incident light level in footcandles Equation (3) can be inverted to determine the intensity of light for a given photoresistance; in conjunction with equation (2), the light intensity can be determined from frequency. Of course, the values given above are provided as examples only for purposes of explanation. Such values are determined on the basis of the particular photoresistor geometry and materials used.

The comparator 204 switches to a high output when Vtime=V/3, Vcomp=V, and Vtrip=2V/3. Capacitor C3 begins to charge with time constant Rphoto*Ctime. When Vtime reaches 2V/3 the comparator switches states to a low output, changing Vcomp to Vcomp=0, and Vtrip to Vtrip= V/3. At this point C3 will discharge through Rphoto. Therefore a 50% duty cycle is established, with the frequency being determined by equation (2). Rphoto varies as a function of incident light, given by equation (3).

C4 is a load capacitor, which causes a voltage across C2 to decrease when the comparator switches states. C4 must be charged from 0 V to Vdc when comparator 204 switches to a high output level state. The current through C4 is supplied by C2, causing the voltage across C2 to decrease. This in turn causes current to flow through rectifier 102a to begin charging capacitor C2, changing the instantaneous load on the tank circuit including internal coil 102d. This load is reflected into the impedance of the external coil 101f as given by equation (1).

Figure 3:
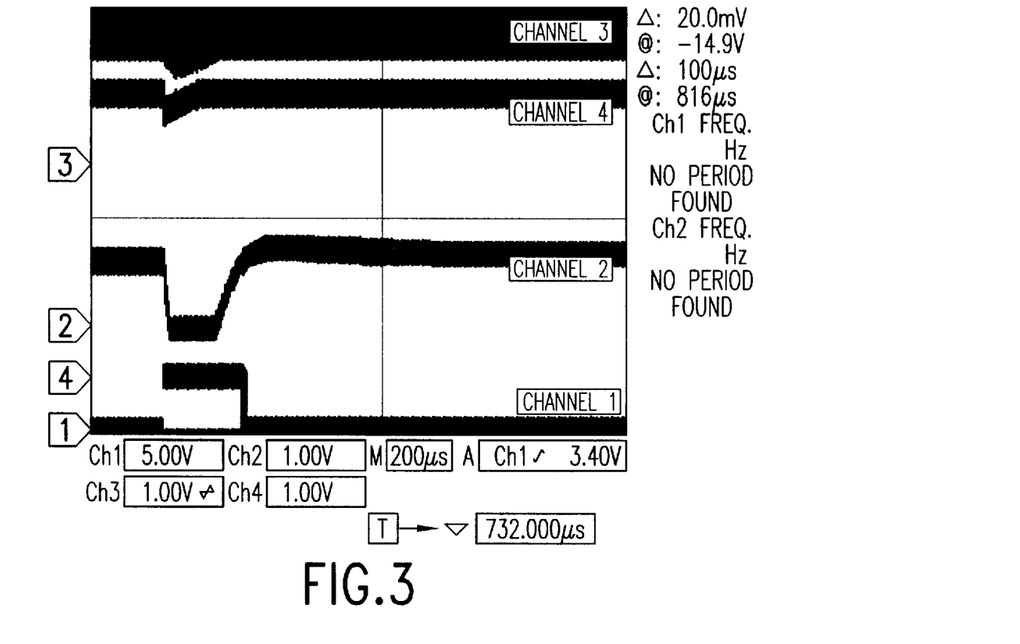
FIGS. 3 and 4 are waveform diagrams illustrating signal waveforms at various points in the sensor device circuit.
Figure 4:
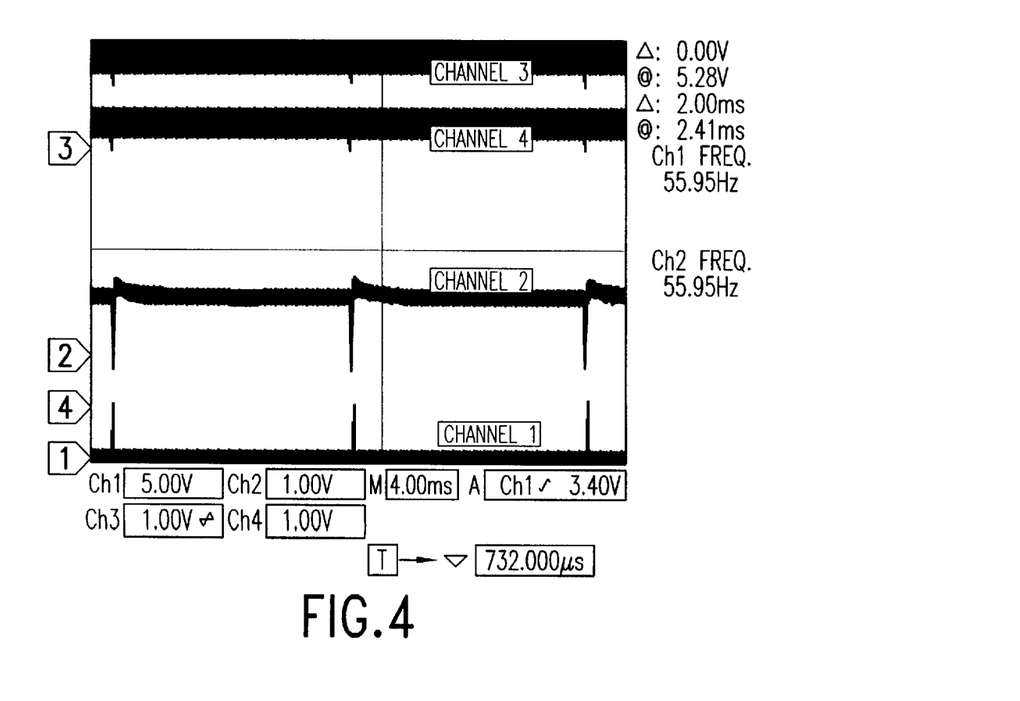

The sensor operation for a single pulse is illustrated in FIG. 3. Channel 4 is the DC voltage on C2, channel 3 shows the same pulse on the external coil 101f, and the output of the AM demodulator is shown at channel 2. Channel 1 shows the output of a comparator which converts the AM demodulator output to a square wave capable of being processed by a digital counter. FIG. 4 shows two complete operation cycles, with the same channel designations indicating the same points in the circuit.

Figure 5A:
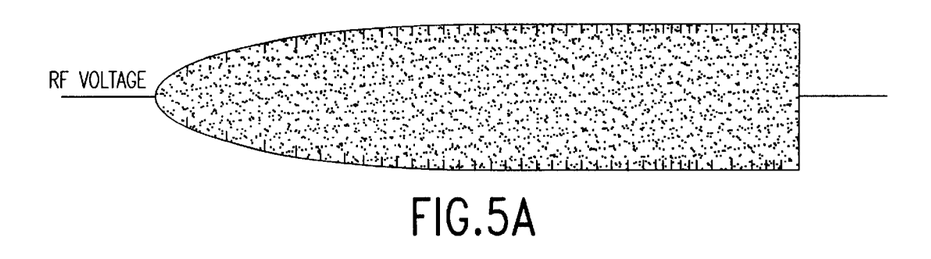
Figure 5B:
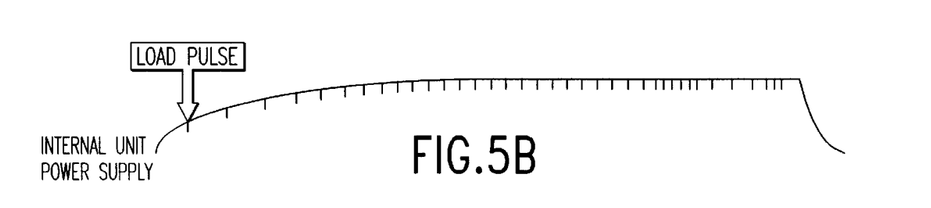
Figure 5C:
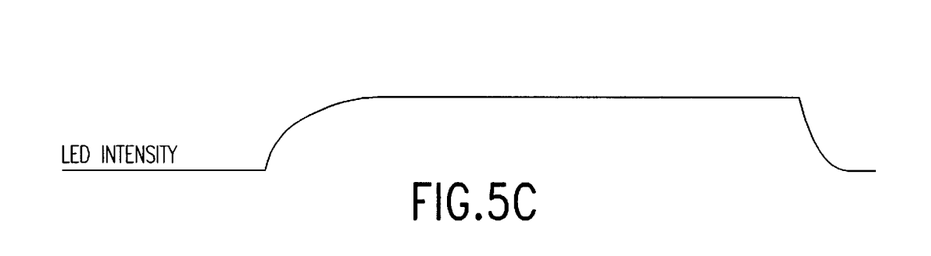
Figure 5D:
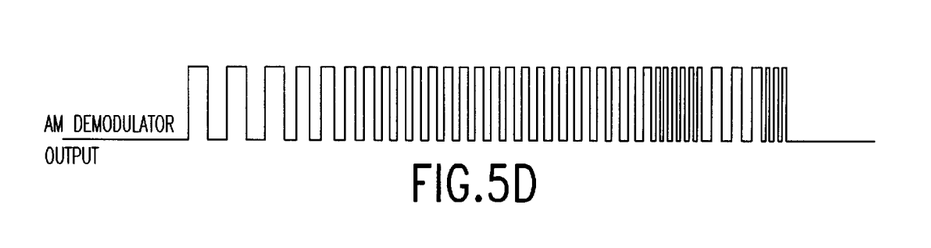
Figure 5E:
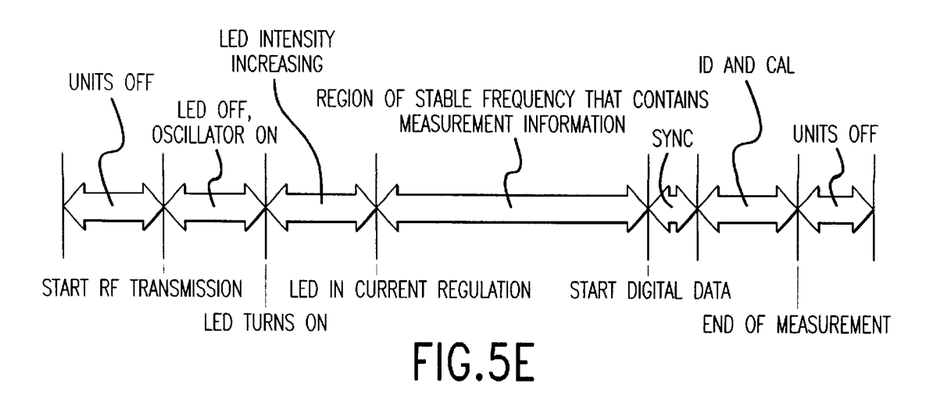

The external unit 101 uses a microprocessor to implement the pulse counter 101c. When sufficient data has been received to obtain a valid reading, the processor shuts down the RF oscillator. FIGS. 5A–5E illustrate timing diagrams for a measurement reading. FIG. 5A shows the envelope of the RF voltage signal applied to the external coil; FIG. 5B shows the waveform of the internal power supply voltage; FIG. 5C shows a waveform of the intensity of LED 202; FIG. 5D shows the output of the AM demodulator 101b; and FIG. 5E shows the timing of the state of circuit operations in accordance with the power supplied to the sensor unit. The internal unit power supply ramps up as the field strength increases. When the power supply output crosses the threshold voltage of the LED plus the feedback voltage, the LED turns on. The AM demodulator output contains the measurement data and digital data in the form of ID codes and other parameters specific to the subject in which the internal unit is implanted. This data is encoded on the RF voltage signal through time division multiplexing of the optoelectronic output with digital identification and parameter storage circuits (not shown). The digital circuits use the RF voltage to generate appropriate clock signals.

The internal storage circuits can store ID codes and parametric values such as calibration constants. This information is returned along with each reading or quantitative measurement. The signals are clocked out by switching from analog pulse train loading to digitally controlled loading at a predefined point in the measurement sequence. This point is detected in the external unit by detecting a predefined bit synchronization pattern in the output data stream. The ID number is used to identify a particular subject and to prevent data corruption when two or more subjects are in the vicinity of the external unit. The calibration factors are applied to the measurement information to obtain analyte levels in clinical units.

Figure 6:
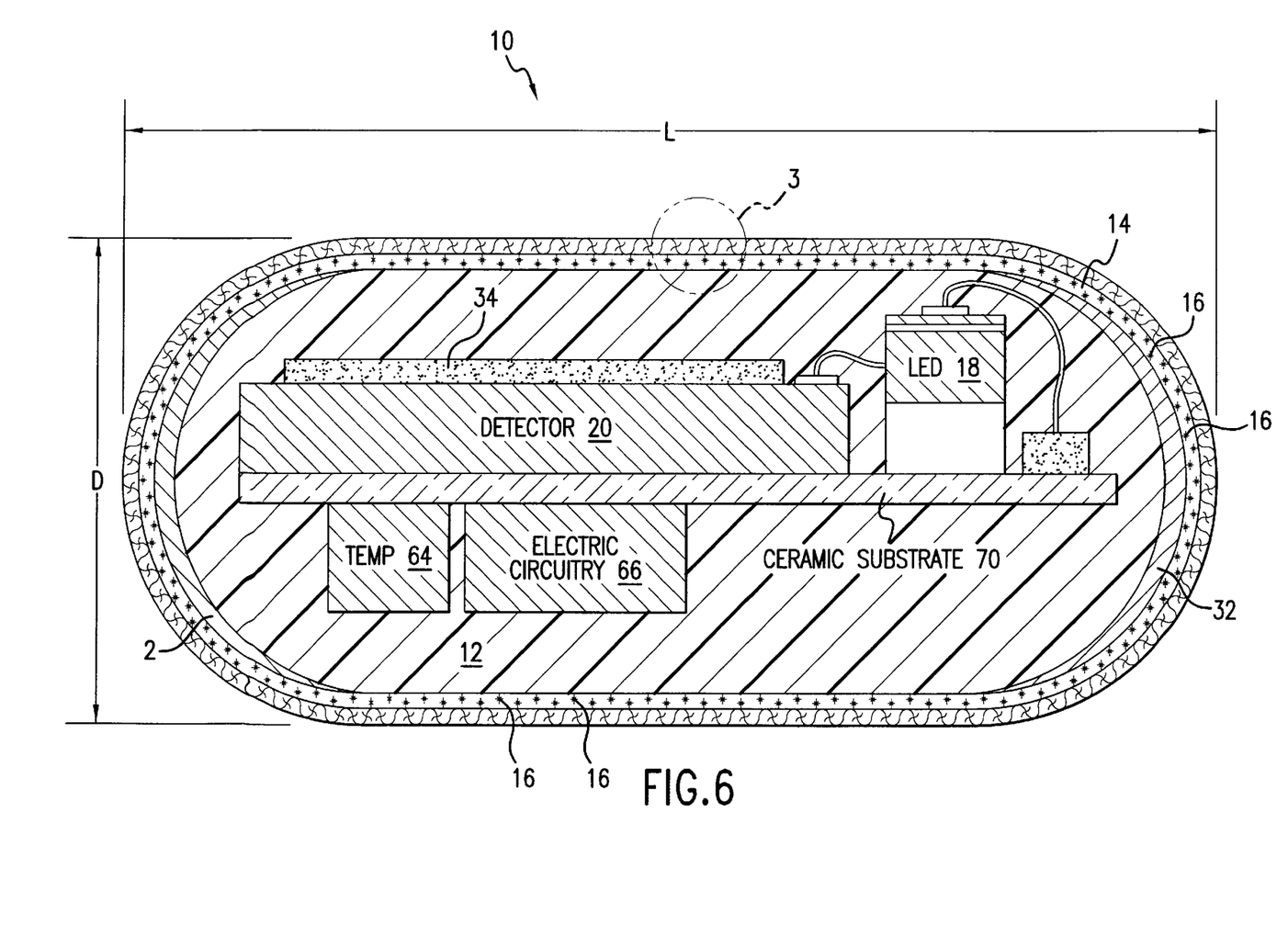
FIG. 6 is a schematic, section view of an implantable fluorescence-based sensor according to the invention.

A sensor 10 according to one aspect of the invention, which operates based on the fluorescence of fluorescent indicator molecules, is shown in FIG. 6. The sensor 10 is composed of a sensor body 12; a matrix layer 14 coated over the exterior surface of the sensor body 12, with fluorescent indicator molecules 16 distributed throughout the layer; a radiation source 18, e.g. an LED, that emits radiation, including radiation over a wavelength or range of wavelengths which interact with the indicator molecules, i.e., in the case of a fluorescence-based sensor, a wavelength or range of wavelengths which cause the indicator molecules 16 to fluoresce; and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules. The sensor 10 further includes a module or housing 66 containing electronic circuitry, and a temperature sensor 64 for providing a temperature reading. In the simplest embodiments, indicator molecules 16 could simply be coated on the surface of the sensor body. In preferred embodiments, however, the indicator molecules are contained within the matrix layer 14, which comprises a biocompatible polymer matrix that is prepared according to methods known in the art and coated on the surface of the sensor body. Suitable biocompatible matrix materials, which must be permeable to the analyte, include methacrylates and hydrogels which advantageously can be made selectively permeable to the analyte.

The sensor body 12 advantageously is formed from a suitable, optically transmissive polymer material which has a refractive index sufficiently different from that of the medium in which the sensor will be used such that the polymer will act as an optical wave guide. Preferred materials are acrylic polymers such as polymethylmethacrylate, polyhydroxypropylmethacrylate and the like, and polycarbonates such as those sold under the trademark Lexan®. The material allows radiation generated by the radiation source 18 (e.g., light at an appropriate wavelength in embodiments in which the radiation source is an LED) and, in the case of a fluorescence-based embodiment, fluorescent light emitted by the indicator molecules, to travel through it. Radiation source or LED 18 corresponds to LED 202 shown in FIG. 2.

Figure 7:
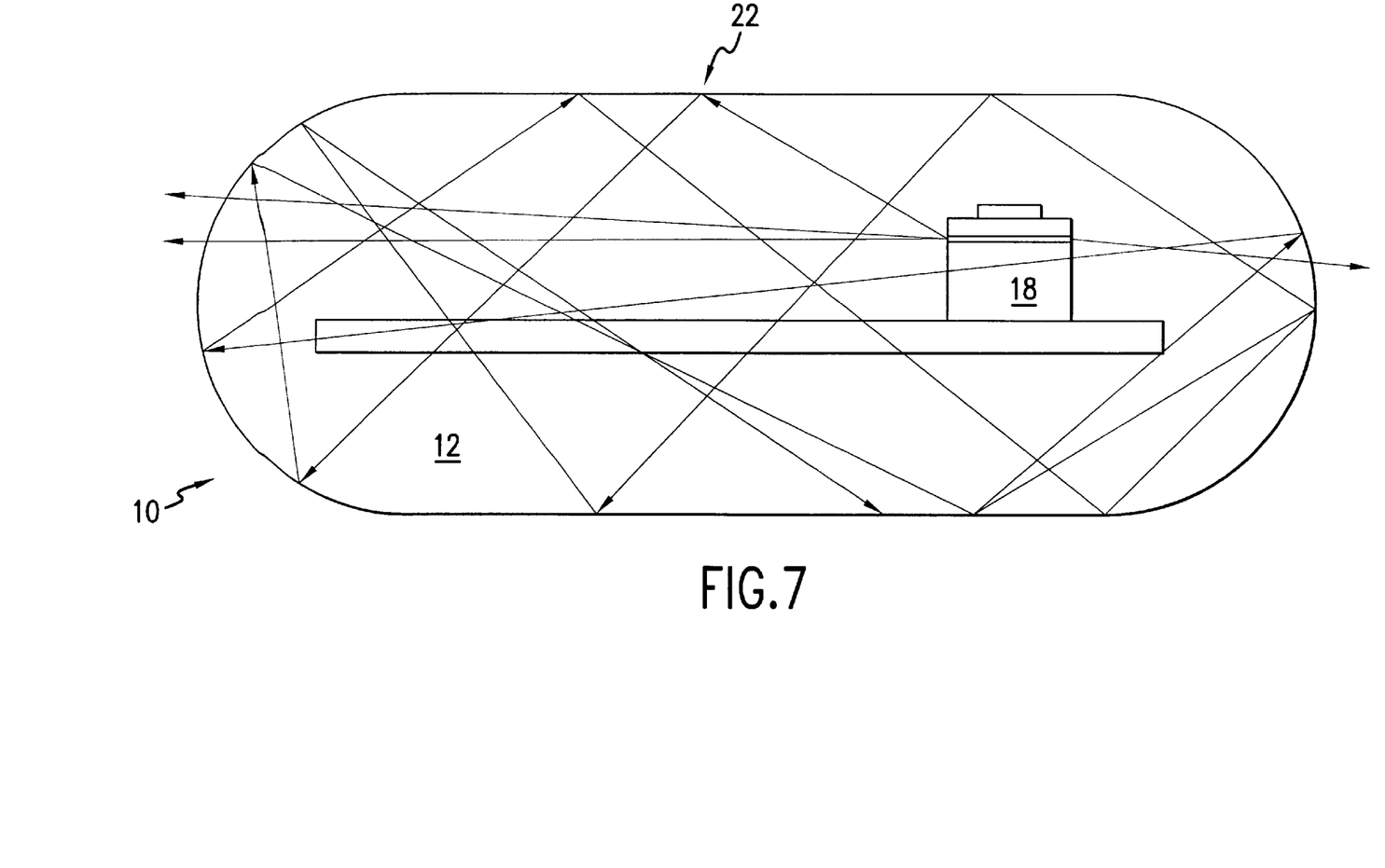
FIG. 7 is a schematic diagram of the fluorescence-based sensor shown in FIG. 6 illustrating the wave guide properties of the sensor.

As shown in FIG. 7, radiation (e.g., light) is emitted by the radiation source 18 and at least some of this radiation is reflected internally at the surface of the sensor body 12, e.g., as at location 22, thereby "bouncing" back-and-forth throughout the interior of the sensor body 12.

It has been found that light reflected from the interface of the sensor body and the surrounding medium is capable of interacting with indicator molecules coated on the surface (whether coated directly thereon or contained within a matrix), e.g., exciting fluorescence in fluorescent indicator molecules coated on the surface. In addition, light which strikes the interface at angles (measured relative to a direction normal to the interface) too small to be reflected passes through the interface and also excites fluorescence in fluorescent indicator molecules. Other modes of interaction between the light (or other radiation) and the interface and the indicator molecules have also been found to be useful depending on the construction of and application for the sensor. Such other modes include evanescent excitation and surface plasma resonance type excitation.

Figure 8:
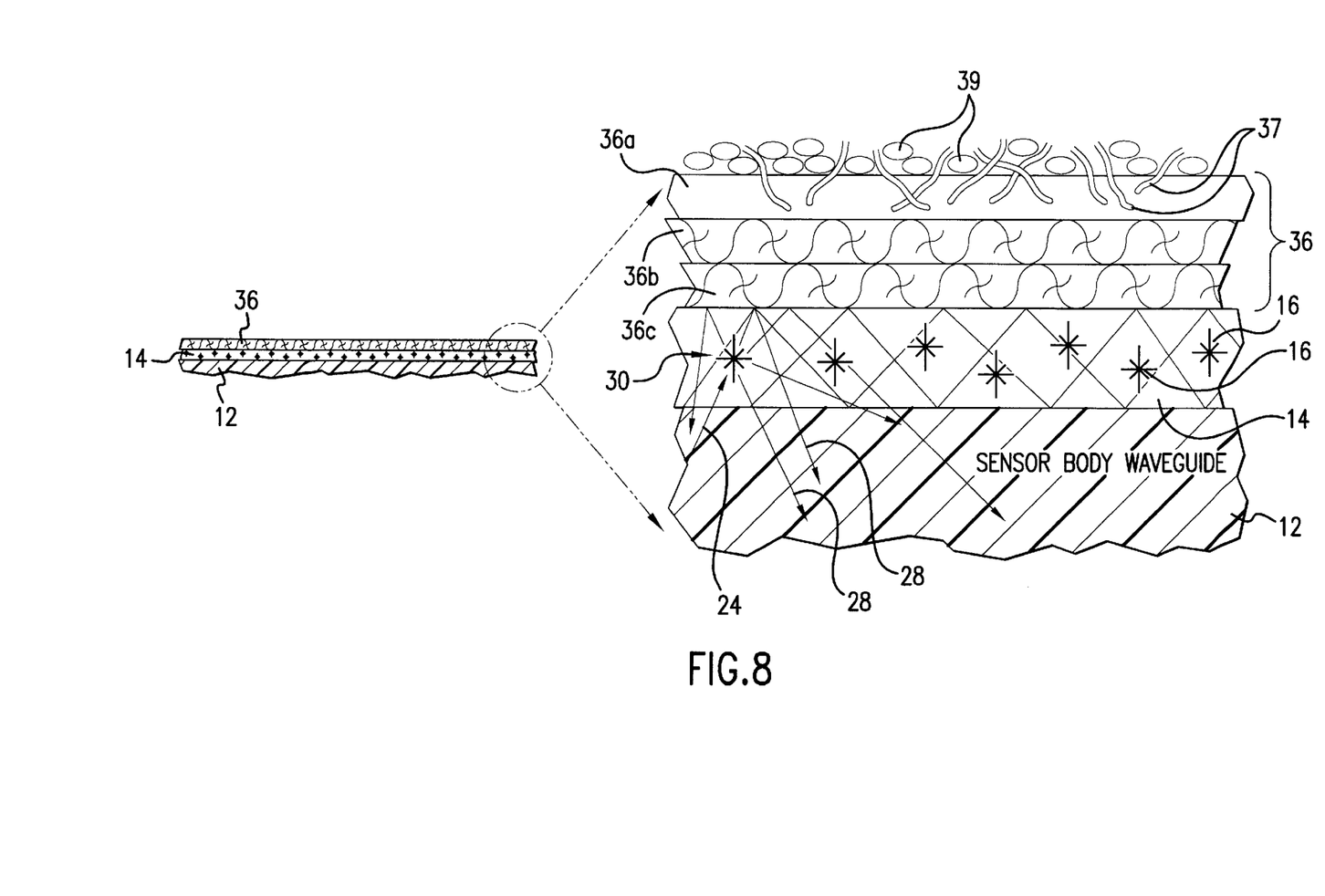
FIG. 8 is a detailed view of the circled portion of FIG. 6 demonstrating internal reflection within the body of the sensor and a preferred construction of the sensor/tissue interface layer.

As demonstrated by FIG. 8, at least some of the light emitted by the fluorescent indicator molecules 16 enters the sensor body 12, either directly or after being reflected by the outermost surface (with respect to the sensor body 12) of the matrix layer 14, as illustrated in region 30. Such fluorescent light 28 is then reflected internally throughout the sensor body 12, much like the radiation emitted by the radiation source 18 is, and, like the radiation emitted by the radiation source, some will strike the interface between the sensor body and the surrounding medium at angles too small to be reflected and will pass back out of the sensor body.

As further illustrated in FIG. 6, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator molecules. The reflective coatings may be formed, for example, from paint or from a metallized material.

An optical filter 34 preferably is provided on the light-sensitive surface of the photodetector 20, which is manufactured of a photosensitive material. Photodetector 20 corresponds to photodetector 203 shown in FIG. 2. Filter 34, as is known from the prior art, prevents or substantially reduces the amount of radiation generated by the source 18 from impinging on the photosensitive surface of the photosensitive element 20. At the same time, the filter allows fluorescent light emitted by fluorescent indicator molecules to pass through it to strike the photosensitive region of the detector. This significantly reduces "noise" in the photodetector signal that is attributable to incident radiation from the source 18.

The application for which the sensor 10 according to one aspect of the invention was developed in particular—although by no means the only application for which it is suitable—is measuring various biological analytes in the human body, e.g., glucose, oxygen, toxins, pharmaceuticals or other drugs, hormones, and other metabolic analytes. The specific composition of the matrix layer 14 and the indicator molecules 16 may vary depending on the particular analyte the sensor is to be used to detect and/or where the sensor is to be used to detect the analyte (i.e., in the blood or in subcutaneous tissues). Two constant requirements, however, are that the matrix layer 14 facilitate exposure of the indicator molecules to the analyte and that the optical characteristics of the indicator molecules (e.g., the level of fluorescence of fluorescent indicator molecules) are a function of the concentration of the specific analyte to which the indicator molecules are exposed.

To facilitate use in-situ in the human body, the sensor 10 is formed, preferably, in a smooth, oblong or rounded shape. Advantageously, it has the approximate size and shape of a bean or a pharmaceutical gelatin capsule, i.e., it is on the order of approximately 300–500 microns to approximately 0.5 inch in length L and on the order of approximately 300 microns to approximately 0.3 inch in depth D, with generally smooth, rounded surfaces throughout. The device of course could be larger or smaller depending on the materials used and upon the intended uses of the device. This configuration permits the sensor 10 to be implanted into the human body, i.e., dermally or into underlying tissues (including into organs or blood vessels) without the sensor interfering with essential bodily functions or causing excessive pain or discomfort.

Moreover, it will be appreciated that any implant placed within the human (or any other animal's) body—even an implant that is comprised of "biocompatible" materials—will cause, to some extent, a "foreign body response" within the organism into which the implant is inserted, simply by virtue of the fact that the implant presents a stimulus. In the case of a sensor 10 that is implanted within the human body, the "foreign body response" is most often fibrotic encapsulation, i.e., the formation of scar tissue. Glucose—a primary analyte which sensors according to the invention are expected to be used to detect—may have its rate of diffusion or transport hindered by such fibrotic encapsulation. Even molecular oxygen (O2), which is very small, may have its rate of diffusion or transport hindered by such fibrotic encapsulation as well. This is simply because the cells forming the fibrotic encapsulation (scar tissue) can be quite dense in nature or have metabolic characteristics different from that of normal tissue.

To overcome this potential hindrance to or delay in exposing the indicator molecules to biological analytes, two primary approaches are contemplated. According to one approach, which is perhaps the simplest approach, a sensor/tissue interface layer—overlying the surface of the sensor body 12 and/or the indicator molecules themselves when the indicator molecules are immobilized directly on the surface of the sensor body, or overlying the surface of the matrix layer 14 when the indicator molecules are contained therein—is prepared from a material which causes little or acceptable levels of fibrotic encapsulation to form. Two examples of such materials described in the literature as having this characteristic are Preclude™ Periocardial Membrane, available from W. L. Gore, and polyisobutylene covalently combined with hydrophiles as described in Kennedy, "Tailoring Polymers for Biological Uses," Chemtech, February 1994, pp. 24–31.

Alternatively, a sensor/tissue interface layer that is composed of several layers of specialized biocompatible materials can be provided over the sensor. As shown in FIG. 8, for example, the sensor/tissue interface layer 36 may include three sublayers 36a, 36b, and 36c. The sublayer 36a, a layer which promotes tissue ingrowth, preferably is made from a biocompatible material that permits the penetration of capillaries 37 into it, even as fibrotic cells 39 (scar tissue) accumulate on it. Gore-Tex® Vascular Graft material (ePTFE), Dacron® (PET) Vascular Graft materials which have been in use for many years, and MEDPOR Biomaterial produced from high-density polyethylene (available from POREX Surgical Inc.) are examples of materials whose basic composition, pore size, and pore architecture promote tissue and vascular ingrowth into the tissue ingrowth layer.

The sublayer 36b, on the other hand, preferably is a biocompatible layer with a pore size (less than 5 micrometers) that is significantly smaller than the pore size of the tissue ingrowth sublayer 36a so as to prevent tissue ingrowth. A presently preferred material from which the sublayer 36b is to be made is the Preclude Periocardial Membrane (formerly called GORE-TEX Surgical Membrane), available from W. L. Gore, Inc., which consists of expanded polytetrafluoroethylene (ePTFE).

The third sublayer 36c acts as a molecular sieve, i.e., it provides a molecular weight cut-off function, excluding molecules such as immunoglobulins, proteins, and glycoproteins while allowing the analyte or analytes of interest to pass through it to the indicator molecules (either coated directly on the sensor body 12 or immobilized within a matrix layer 14). Many well known cellulose-type membranes, e.g., of the sort used in kidney dialysis filtration cartridges, may be used for the molecular weight cut-off layer 36c.

As will be recognized, the sensor as shown in FIG. 6 is wholly self-contained such that no electrical leads extend into or out of the sensor body, either to supply power to the sensor (e.g., for driving the source 18) or to transmit signals from the sensor. All of the electronics illustrated in FIG. 2 may be housed in a module 66 as shown in FIG. 6.

As also will be recognized, the fluorescence-based sensor embodiments described in FIGS. 6–8 are just examples to which the disclosed invention may be applied. The present invention may also be applied in a number of other applications such as, for example, an absorbance-based sensor or a refractive-index-based sensor as described in U.S. Pat. No. 6,330,464, incorporated herein by reference.

The invention having been thus described, it will be apparent to those skilled in the art that the same may be varied in many ways without departing from the spirit and scope of the invention. For example, while the invention has been described with reference to an analog circuit, the principles of the invention may be carried out equivalently through the use of an appropriately programmed digital signal processor. Any and all such modifications are intended to be encompassed by the following claims.

What is claimed is:

1. Apparatus for retrieving information from a sensor device, comprising:

an internal sensor unit for taking quantitative analyte measurements, including a first coil forming part of a power supply for said sensor unit, a load coupled to said first coil, and a sensor circuit for modifying said load in accordance with sensor measurement information obtained by said sensor circuit;

an external unit including a second coil which is mutually inductively coupled to said first coil upon said second coil being placed within a predetermined proximal distance from said first coil, an oscillator for driving said second coil to induce a charging current in said first coil, and a detector for detecting variations in a load on said second coil induced by changes to said load in said internal sensor unit and for providing information signals corresponding to said load changes; and a processor for receiving and processing said information signals.

2. Apparatus according to claim 1, wherein said sensor circuit comprises an indicator element which emits radiation in proportion to levels of said analyte.

3. Apparatus according to claim 2, wherein said load comprises a photosensitive resistor which receives radiation from said indicator element.

4. Apparatus according to claim 2, wherein said sensor circuit further comprises a radiation source for emitting electromagnetic radiation which stimulates emission of radiation.

5. Apparatus according to claim 2, wherein said indicator element emits fluorescent radiation in proportion to levels of said analyte.

6. Apparatus according to claim 3, wherein said load comprises a photosensitive resistor which receives fluorescent radiation from said indicator element.

7. Apparatus according to claim 4, wherein said radiation source for emitting electromagnetic radiation stimulates emission of fluorescent radiation.

8. Apparatus according to claim 1, wherein said internal unit is implantable in the body of a mammal.

9. Apparatus according to claim 1, wherein said power supply further includes a charging capacitor which is charged by said charging current.

10. Apparatus according to claim 1, wherein said detector of said external unit includes an amplitude modulation (AM) demodulator for detecting changes in amplitude of a voltage waveform caused by changes in said load, said voltage waveform being inductively reflected into said second coil through said first coil.

11. Apparatus according to claim 10, wherein said external unit further includes a pulse counter for converting said detected changes in waveform amplitude into pulses suitable for being converted into computer-readable form.

12. Apparatus according to claim 11, wherein said processor includes a computer.

13. Apparatus according to claim 1, wherein said internal unit is ingestible in the body of a mammal.

14. Apparatus according to claim 1, wherein said internal unit is implantable in the body of a fish.

15. Apparatus according to claim 1, wherein said internal unit is implantable in the body of a plant.

16. Apparatus according to claim 1, wherein said sensor circuit comprises an indicator element which absorbs radiation in proportion to levels of said analyte.

17. A sensor device for detecting the presence or concentration of an analyte in a medium, comprising:

an enclosed sensor body having an outer surface surrounding said sensor body;

a radiation source in said sensor body which emits radiation within said sensor body;

an indicator element having an optical characteristic that is affected by the presence or concentration of an analyte, said indicator element being positioned on said sensor body to receive radiation that travels from said radiation source, and which transmits radiation into said sensor body;

a photosensitive element located in said sensor body and positioned to receive radiation within the sensor body from said indicator element; and an inductive element located in said sensor and coupled to said photosensitive element, said inductive element being adapted to receive from an external inductive element a magnetically induced electric current for supplying power to said sensor device, and being further adapted to induce in said external inductive element an electric current which changes as a function of the amount of radiation received by said photosensitive element.

\* \* \* \* \*